United States Patent
Volkmuth et al.

(10) Patent No.: US 9,907,490 B2
(45) Date of Patent: Mar. 6, 2018

(54) LANCING DEVICE FOR TAKING BLOOD SAMPLES

(71) Applicant: Gerresheimer Regensburg GmbH, Regensburg (DE)

(72) Inventors: Julia Volkmuth, Maxhuette-Haidhof (DE); Michael Strehl, Pfreimd (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 140 days.

(21) Appl. No.: 14/360,525

(22) PCT Filed: Nov. 26, 2012

(86) PCT No.: PCT/EP2012/073579
§ 371 (c)(1),
(2) Date: May 23, 2014

(87) PCT Pub. No.: WO2013/092115
PCT Pub. Date: Jun. 27, 2013

(65) Prior Publication Data
US 2014/0288585 A1 Sep. 25, 2014

(30) Foreign Application Priority Data
Dec. 19, 2011 (DE) .......................... 10 2011 056 626

(51) Int. Cl.
*A61B 5/15* (2006.01)
*A61B 5/151* (2006.01)

(52) U.S. Cl.
CPC .......... *A61B 5/1411* (2013.01); *A61B 5/1513* (2013.01); *A61B 5/1519* (2013.01);
(Continued)

(58) Field of Classification Search
CPC ............ A61B 5/1411; A61B 5/150022; A61B 5/15117; A61B 5/150412; A61B 5/15186;
(Continued)

(56) References Cited

U.S. PATENT DOCUMENTS 6,015,392 A * 1/2000 Douglas ............... A61B 5/1411
600/573
6,045,567 A 4/2000 Taylor et al.
(Continued)

FOREIGN PATENT DOCUMENTS

AU 6069686 2/1987
CN 1222840 7/1999
(Continued)

OTHER PUBLICATIONS

International Search Report, dated Jan. 4, 2013, corresponding to International Application No. PCT/EP2012/073579 (filed Nov. 26, 2012), 12 pp.
(Continued)

*Primary Examiner* — Eric Rosen
*Assistant Examiner* — Mikail Mannan
(74) *Attorney, Agent, or Firm* — Lathrop Gage LLP

(57) ABSTRACT

A lancing device comprising a lancet holder for holding an exchangeable lancet and comprising a drive element for driving the lancet holder. The drive element has two spring elements comprising a lancing spring element for accelerating the lancet holder in the lancing direction and a restoring spring element for accelerating the lancet holder counter to the lancing direction. The drive element has a carriage unit with a spring-tensioning carriage part and a lancing carriage part, and the spring-tensioning carriage part and the lancing carriage part are arranged to be displaceable in translation relative to one another and form a lancing spring element receiving region and a restoring spring element
(Continued)

Figure 1:
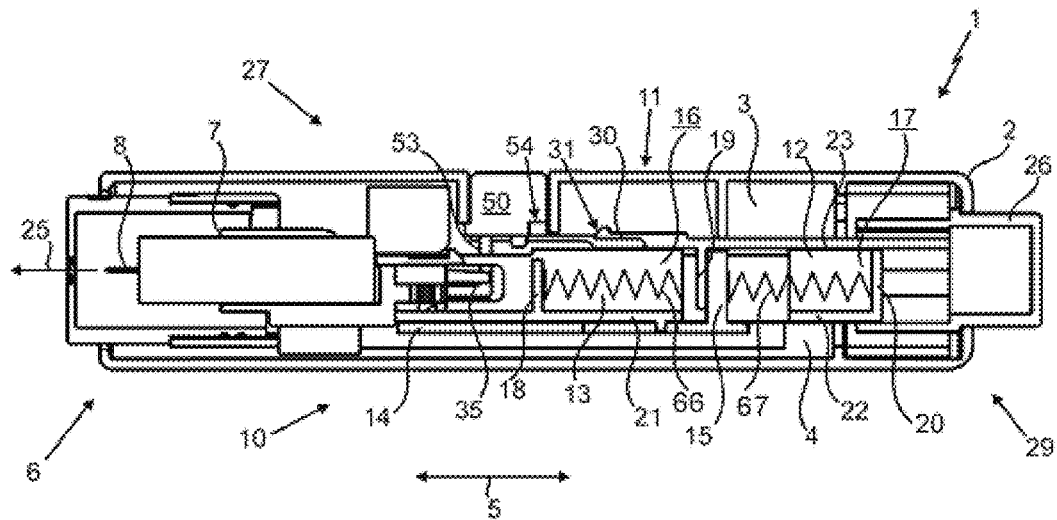

receiving region. The lancing spring element receiving region can be reduced by translational displacement of the spring-tensioning carriage part relative to the lancing carriage part, in order to pre-tension the lancing spring element within the lancing spring element receiving region.

14 Claims, 4 Drawing Sheets

(52) U.S. Cl.
CPC .... *A61B 5/150022* (2013.01); *A61B 5/15113* (2013.01); *A61B 5/15117* (2013.01); *A61B 5/15196* (2013.01); *A61B 5/150412* (2013.01); *A61B 5/150503* (2013.01)

(58) Field of Classification Search
CPC ............ A61B 5/15142; A61B 5/15146; A61B 5/15188; A61B 17/32093; A61B 5/150381; A61B 5/150167; A61B 5/150297; A61B 5/150374; A61B 5/155; A61B 5/157; A61B 5/151
USPC .......................................................... 606/181
See application file for complete search history.

(56) References Cited

U.S. PATENT DOCUMENTS

| | | | |
|---|---|---|---|
| 6,730,046 B1* | 5/2004 | Hamamoto | A61B 5/150022 606/182 |
| 8,827,925 B2 | 9/2014 | Butz et al. | |
| 8,828,039 B2 | 9/2014 | Butz et al. | |
| 8,986,258 B2 | 3/2015 | Michaelis | |
| D740,422 S | 10/2015 | Herfort | |
| 9,314,200 B2 | 4/2016 | Vogl et al. | |
| 2005/0085839 A1* | 4/2005 | Allen | A61B 5/1411 606/181 |
| 2008/0195132 A1* | 8/2008 | Schraga | A61B 5/1411 606/182 |
| 2009/0030442 A1* | 1/2009 | Potter | A61B 5/1411 606/182 |
| 2009/0125048 A1 | 5/2009 | Robbins et al. | |
| 2014/0081173 A1 | 3/2014 | Volkmuth et al. | |
| 2014/0100481 A1 | 4/2014 | Volkmuth et al. | |
| 2014/0100482 A1 | 4/2014 | Volkmuth et al. | |
| 2014/0128897 A1 | 5/2014 | Butz et al. | |
| 2014/0155926 A1 | 6/2014 | Volkmuth et al. | |

FOREIGN PATENT DOCUMENTS

| | | |
|---|---|---|
| CN | 1462608 | 12/2003 |
| CN | 1473022 | 2/2004 |
| CN | 1993079 | 7/2007 |
| EP | 0212906 | 3/1987 |
| EP | 0885590 | 12/1998 |
| EP | 1060707 | 12/2000 |
| WO | 2011/044971 | 4/2011 |

OTHER PUBLICATIONS

Chinese First Office Action, dated Jun. 26, 2015, in Chinese Patent Application No. 201280058604.0, a related application, 10 pp. (with English translation).

* cited by examiner

LANCING DEVICE FOR TAKING BLOOD SAMPLES

CROSS-REFERENCE TO RELATED APPLICATIONS

This application is a U.S. National Stage Application filed under 35 U.S.C. § 371 of International Application No. PCT/EP2012/073579, filed Nov. 26, 2012, which claims the benefit of German Application No. 10 2011 056 626.0, filed Dec. 19, 2011. Both of these applications are hereby incorporated by reference in their entireties.

DESCRIPTION

The invention relates to a lancing device for taking blood samples, comprising a lancet holder for holding an exchangeable lancet and comprising a drive means for driving the lancet holder, in which the drive means has two spring elements comprising a lancing spring element for accelerating the lancet holder in the lancing direction and a restoring spring element for accelerating the lancet holder counter to the lancing direction.

Generic lancing devices comprising a drive means consisting of in particular two spring elements connected in series are already known from the prior art. In a lancing device which is configured in such a way, a front lancing spring element, i.e. a spring element facing a lancet holder which is to be accelerated, provides for acceleration of the lancet holder during a lancing operation with a lancet which is held by the lancet holder. A rear restoring spring element, i.e. a spring element which is remote from the lancet holder which is to be accelerated, provides for a restoring movement of the lancet holder after the lancing operation. Due to these two active spring elements, excessive critical subsequent oscillation of the lancet holder on the lancing device after a lancing operation can be readily avoided.

It is an object of the present invention to simplify generic lancing devices once again with regard to their construction and furthermore with regard to operability.

The object of the invention is achieved by a lancing device for taking blood samples, comprising a lancet holder for holding an exchangeable lancet and comprising a drive means for driving the lancet holder, in which the drive means has two spring elements comprising a lancing spring element for accelerating the lancet holder in the lancing direction and a restoring spring element for accelerating the lancet holder counter to the lancing direction, and in which the drive means has a carriage unit with a spring-tensioning carriage part and with a lancing carriage part, and the spring-tensioning carriage part and the lancing carriage part are arranged to be displaceable in translation relative to one another and form a lancing spring element receiving region and a restoring spring element receiving region, and the lancing spring element receiving region can be reduced by translational displacement of the spring-tensioning carriage part relative to the lancing carriage part in order to pretension the lancing spring element within the lancing spring element receiving region for a forthcoming lancing operation, the spring-tensioning carriage part being arranged to be movable manually by a tensioning actuation element from outside the lancing device.

Due to the fact that the present lancing spring element by means of the spring-tensioning carriage part is pretensionable, which is displaceable in translation and axially and can be moved axially by the actuating tensioning element from outside the lancing device, the drive means can be prepared for the next lancing operation very simply overall in design terms.

Furthermore, it is advantageously not necessary for the spring elements to over-oscillate, since a forwards movement during the lancing operation and the backwards movement following it after the proper lancing operation are carried out by two separate spring elements.

Advantageously, the two spring elements are connected in series. Depending on the configuration of the lancing device, they may however also be arranged acting coaxially or respectively parallel to each other.

The lancing spring element receiving region and respectively the restoring spring element receiving region can be realised structurally in many different ways. Preferably they are configured as lancing spring element chambers or as restoring spring element chambers respectively, in which the spring elements can advantageously be held within the lancing device at least partially in each case both axially and radially.

One particularly preferred variant provides for the lancing device to comprise a triggering actuation element for triggering the lancing operation which is mounted such that the lancing carriage part and the spring-tensioning carriage part can be unlocked sequentially. This means that the movable mechanism of the present lancing device can be constructed and actuated particularly compactly.

Advantageously, the lancing carriage part and the spring-tensioning carriage part have a common triggering actuation element, so that the lancing device can be constructed with extremely reduced components.

It goes without saying that the present triggering actuation element can be configured in many different ways. Preferably it is designed as a radially displaceable pressing element. It may however also be no less advantageously configured as a slide element which is mounted in the housing to be axially slidable in the longitudinal extension of the lancing device.

With regard to a very good geometric arrangement and/or functional splitting of the lancing carriage part and the spring-tensioning carriage part, it is advantageous if the triggering actuation element, relative to the longitudinal extension of the lancing device, is arranged approximately centrally radially externally on the peripheral surface of the housing.

Furthermore, it is advantageous if the triggering actuation element is displaceable manually out of a parking position into a triggering position in which both the lancing carriage part and the spring-tensioning carriage part are unlocked, the spring-tensioning carriage part in the triggering position of the triggering actuation element being held in the tensioning position by the triggering actuation element. This means that it can be ensured that the spring-tensioning carriage part remains in the tensioning position for a sufficiently long time, namely until the lancing operation is successfully ended. Thus a spring force of the lancing spring element which is sufficiently high for the lancing operation can be ensured.

The lancing carriage part and the spring-tensioning carriage part can be triggered extremely easily in design terms by the sole triggering actuation element if the triggering actuation element is arranged radially in front of a latching element of the spring-tensioning carriage part and in front of a holding element of the lancing carriage part such that, owing to the triggering actuation element, firstly the latching element is arranged to be displaceable out of its latching position and secondly the holding element is arranged to be displaceable out of a holding position.

In this respect, a further very advantageous variant provides for the spring-tensioning carriage part to comprise a latching element for latching in a tensioning position in which the lancing spring element is pre-tensioned such that the lancing carriage part can be accelerated for the lancing operation, and the lancing carriage part comprises a holding element for holding the lancing carriage part in a different tensioning position, in which the lancing spring element is pre-tensioned such that the lancing carriage part can be accelerated for the lancing operation, the latching element and the holding element being arranged axially directed at each other. Due to this placing of the latching element and the holding element head-to-head in a structurally narrow space, the design of the lancing device can be further advantageously simplified.

In order to be able to hold the spring-tensioning carriage part reliably in the tensioning position, it is advantageous if the latching element can be latched on a latching edge of a housing of the lancing device.

If the holding element is mounted to be guided both radially and axially along a sliding means, the sliding means being arranged adjacent to the lancing carriage part, the holding element can be purposefully actuated particularly reliably and guided within the lancing device on a component which is different from the lancing carriage part.

Preferably the sliding means is arranged in the housing of the lancing device. Ideally, the sliding means has an L-shaped groove path.

At this point, it should be pointed out that the features in conjunction with the triggering actuation element likewise advantageously develop known lancing devices even without the rest of the features of the invention. In this respect, the features in relation to this, independently of the other features, are advantageous in particular with regard to the present lancing device.

The lancing device can be further simplified in design terms if the lancing spring element receiving region is limited at the front by an axially slidable lancing carriage part partition and at the rear by an axially slidable spring carriage part partition. This means that cooperation of the lancing carriage part and of the spring-tensioning carriage part can be jointly realised particularly simply in structural terms.

If the spring-tensioning carriage part is arranged mounted at least partially within the lancing carriage part, they can advantageously be pushed into one another, as a result of which the reduction of the receiving region described at the beginning can be brought about with a compact construction.

It is particularly advantageous that the present kinematics of the drive means with regard to the tensioning operation and to the proper lancing operation are implemented substantially by the spring-tensioning carriage part and the lancing carriage part, which are arranged slidably in one another, the spring-tensioning carriage part and respectively the lancing carriage part in each case having a different function depending on the current operating position.

A further structural simplification of the lancing device can be achieved if the lancing device has a two-part housing with an upper shell part and a lower shell part, on which parts the lancing carriage part and the spring-tensioning carriage part are guided in translation relative to each other and are arranged to be temporarily storable.

Furthermore, it is advantageous if the tensioning actuation element is arranged axially behind the carriage unit on an end of the lancing device which is remote from the lancet holder, and the triggering actuation element is arranged radially next to the carriage unit.

While the triggering actuation element is preferably arranged as described above on the peripheral surface of the housing, it is advantageous with regard to the tensioning actuation element if the latter is arranged approximately centrally on the housing relative to the diameter of the lancing device. In this arrangement, the spring-tensioning carriage part can be displaced axially within the lancing device and relative to the lancing carriage part intuitively by a user of the lancing spring element for pre-tensioning purposes.

It goes without saying that the present tensioning actuation element can also be configured in many different ways. Preferably it is designed as an axially displaceable pressing element. It may however also be no less advantageously configured as a slide element which is arranged radially on the peripheral surface and which is mounted in the housing to be axially slidable in the longitudinal extension of the lancing device.

Overall, extremely good ergonomic handling on one hand owing to the simple tensioning of the lancing spring element by pressing the tensioning actuation element and on the other hand owing to the simple triggering of the lancing carriage part by pressing the triggering actuation element can be achieved with the lancing device according to the invention.

At this point it should be pointed out that in particular this simple handling is implemented advantageously in design terms by means of the drive means with a dual spring oscillation system comprising the lancing spring element and the restoring spring element, and with a sliding mechanism which is of simple construction and is virtually fail-safe. Advantageously, a curved-path mechanism can be dispensed with in the present case.

Figure 2:
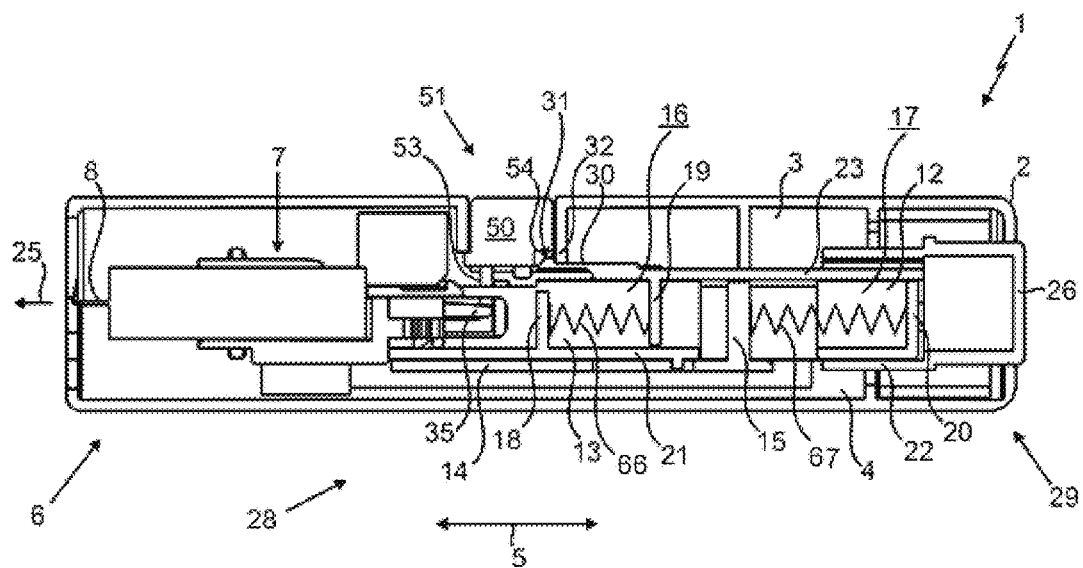
Figure 3:
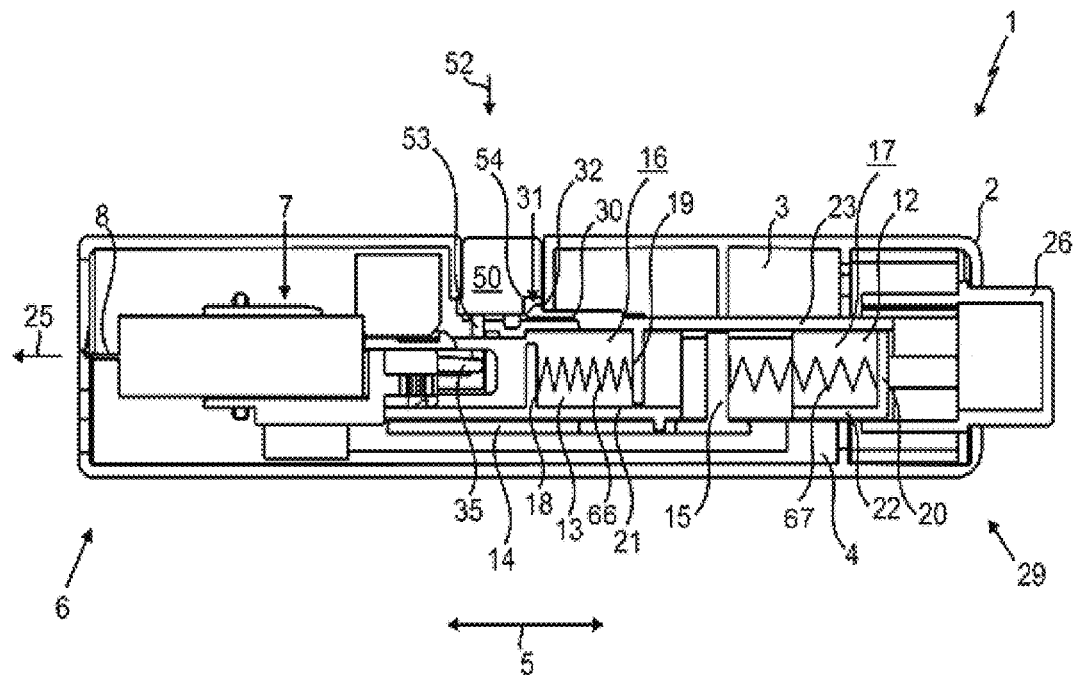
Figure 4:
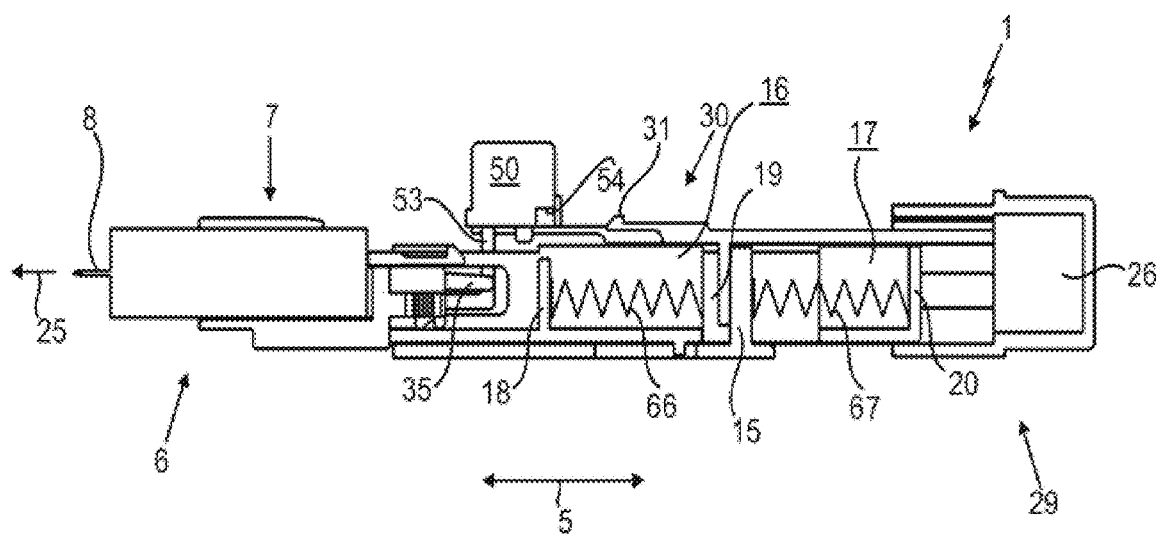
Figure 5:
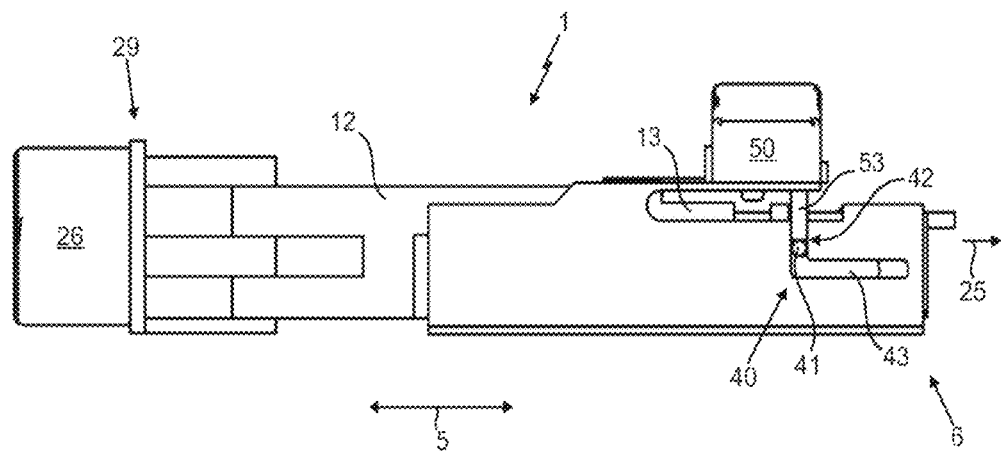
Figure 6:
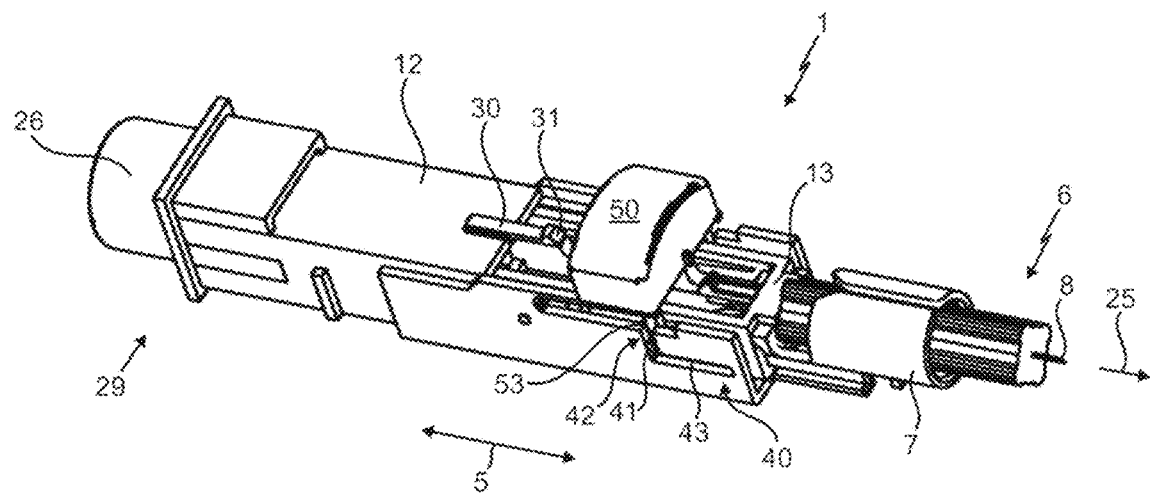
Figure 7:
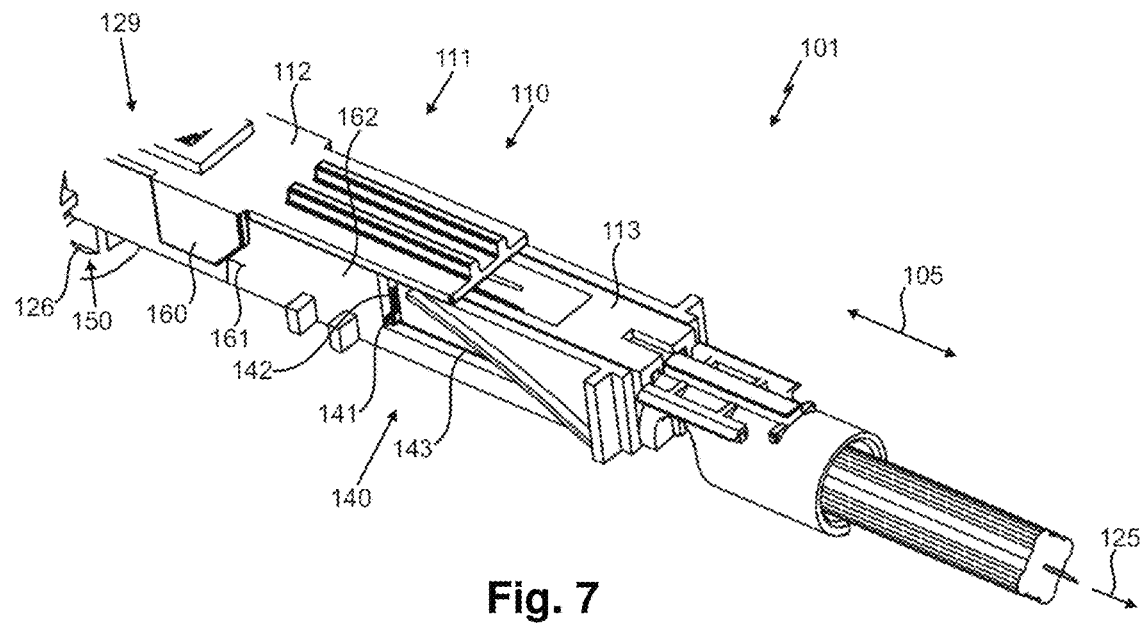
Figure 8:
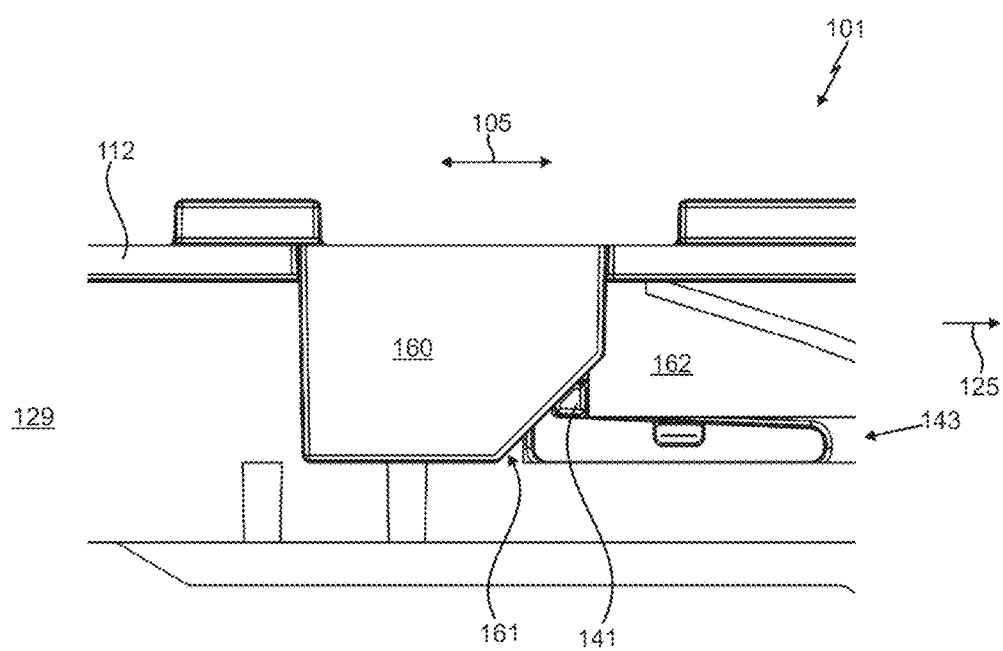

Further advantages, aims and properties of the present invention will be explained with reference to the appended drawings and the subsequent description, in which by way of example a lancing device according to the invention is illustrated and described. The drawings depict:

FIG. 1 diagrammatically, a longitudinal sectional view of a lancing device in a starting position;

FIG. 2 diagrammatically, a further longitudinal sectional view of the lancing aid of FIG. 1 in a tensioning position in which the lancing spring is pre-tensioned;

FIG. 3 diagrammatically, a longitudinal sectional view of the lancing aid of FIGS. 1 and 2 in a triggering position, in which the lancing device is triggered;

FIG. 4 diagrammatically, a first side view of the lancing device of FIGS. 1 to 3;

FIG. 5 diagrammatically, a second side view of the lancing device of FIGS. 1 to 4;

FIG. 6 diagrammatically, a perspective view of the lancing device of FIGS. 1 to 5;

FIG. 7 diagrammatically, a perspective bottom view of a further lancing device with an alternative triggering actuation element; and FIG. 8 diagrammatically, a detail view of the triggering actuation element of FIG. 7.

The lancing device 1 shown in FIGS. 1 to 8 is intended for taking blood samples. The lancing device 1 has a two-part housing 2 with an upper shell part 3 and a lower shell part 4, and with a longitudinal extension 5.

On the front side 6 of the lancing device 1 there is provided a multi-compatible lancet holder 7 for holding a lancet 8. Behind it is placed a drive means 10 with a carriage unit 11 comprising a spring-tensioning carriage part 12 and a lancing carriage part 13.

The spring-tensioning carriage part 12 and the lancing carriage part 13 are on one hand arranged guided axially slidably along the longitudinal extension 5 in the housing 2 by corresponding guide webs 14 and 15 (here shown and numbered only as an example). On the other hand, the spring-tensioning carriage part 12 and the lancing carriage part 13 are arranged in the housing 2 to be displaceable in translation relative to each other.

The spring-tensioning carriage part 12 and the lancing carriage part 13 form a lancing spring element receiving region 16 for receiving a lancing spring element 66, and a restoring spring element receiving region 17 for receiving a restoring spring element 67.

The lancing spring element and the restoring spring element in this case are arranged in a series connection in the drive device 10. In this respect, an advantageous dual spring oscillation system (not explicitly numbered) is provided with the drive device 10.

The lancing carriage part 13 in this case is in an operative connection with the lancet holder 7 such that the lancet holder 7 is accelerated by means of the lancing carriage part 13 if the lancing device 1 is triggered, as is still to be described below.

The spring-tensioning carriage part 12 within the meaning of the invention serves substantially only for the tensioning, which in design terms is very simple, of the lancing spring element 66.

Whereas the lancing spring element receiving region 16 is axially limited by a front transverse wall 18 of the lancing carriage part 13 and a transverse wall 19 of the spring-tensioning carriage part 12, the restoring spring element receiving region 17 is axially chambered by a rear transverse wall 20 of the lancing carriage part 13 and the guide web 15 of the housing 2.

Radially laterally, the lancing spring element receiving region 16 and the restoring spring element receiving region 17 are at least partially limited by longitudinal walls 21 and 22 of the lancing carriage part 13 and by a further longitudinal wall 23 of the spring-tensioning carriage part 12. Further corresponding limiting longitudinal walls are not numbered here for clarity.

Furthermore, the lancing spring element receiving region 16 can be made smaller relative to the lancing carriage part 13 by translational displacement of the spring-tensioning carriage part 12 in the lancing direction 25, in order to pre-tension the lancing spring element within the lancing spring element receiving region 16 for a forthcoming lancing operation, the spring-tensioning carriage part 12 being arranged to be movable manually from a starting position 27 (see FIG. 1) into a general tensioning position 28 (see FIG. 2) of the lancing device 1 by a tensioning actuation element 26 from outside the lancing device 1.

The tensioning actuation element 26 is arranged on the rear side 29 of the lancing device 1 so as to be able to be actuated manually directly accessibly from the outside, said tensioning actuation element being pressed into the housing 2 along the longitudinal extension 5 and in the lancing direction 25, in order to be able to pre-tension the lancing spring element in a suitable manner.

In this tensioning position 28, a latching element 30 of the spring-tensioning carriage part 12 latches into a latching position with its latching projection 31 on a latching edge 32 of the housing 2, so that the spring-tensioning carriage part 12 is held securely in the tensioning position 28 counter to the spring force of the lancing spring element.

In this tensioning position 28, the lancing carriage part 13 is fixed by means of a holding element 35 in a sliding means 40 which is provided in the housing 2 adjacent to the lancing carriage part 13.

In the tensioning position 28, a spring part 41 of the holding element 35 is located in a first groove portion 42 of the sliding means 40. The first groove portion 42 in this case runs transversely to the longitudinal extension 5 of the lancing device 1.

Furthermore, the sliding means 40 also comprises a further groove portion 43 which is arranged at a right angle to the first groove portion 42 and is aligned with the longitudinal extension 5 (see in particular FIGS. 5 and 6).

In this respect, the holding element 35 and hence also the lancing carriage part 13 is axially fixed on the sliding means 40 as long as the spring part 41 is located in the first groove portion 42 and not in the second groove portion 43.

Furthermore, the lancing device 1 has a triggering actuation element 50 for triggering the lancing operation which is mounted in the housing 2 of the lancing device 1 such that the lancing carriage part 13 and the spring-tensioning carriage part 12 can be unlocked sequentially.

For this, the triggering actuation element 50 is arranged radially externally approximately centrally on the housing 2 of the lancing device 1 such that at least in the tensioning position 27 it is placed both above the latching projection 31 of the latching element 30 and above the spring part 41 of the holding element 35.

The triggering actuation element 50 within the meaning of the invention has an internal contour (not numbered separately here for clarity) which is constructed such that the holding element 35 and the latching element 30 are actuated sequentially by means of the triggering actuation element 50 if the triggering actuation element 50 is pressed from its parking position 51 (see in particular FIG. 2) into a triggering position (not explicitly illustrated here) in the radial direction 52 (see in particular FIG. 3).

To actuate the holding element 35, the triggering actuation element 50 has an actuating finger element 53 which projects radially further into the lancing device 1.

To actuate the latching element 30, the triggering actuation element 50 has an actuating edge 54 which is set back further radially than the actuating finger element 53.

According to the illustration of FIG. 1, the tensioning actuation element 26 has not yet been pressed in the lancing direction 25. In this respect, the latching element 30 is also not yet latched on the housing 2. Thus, the lancing device 1 is still in the starting position 27, in which the lancing spring element in the lancing spring element receiving region 16 is not yet sufficiently pre-tensioned for a lancing operation.

According to the illustration of FIG. 2, the tensioning actuation element 26 and hence also the spring-tensioning carriage part 12 is pressed along the longitudinal extension 5 in the lancing direction 25 and into the housing 2 such that the latching projection 31 of the latching element 30 of the spring-tensioning carriage part 12 can snap in behind the latching edge 32 of the housing 2, as a result of which the spring-tensioning carriage element 12 is axially fixed to the housing 2 and the lancing spring element is pre-tensioned.

During this, the holding element 35 of the lancing carriage part 13 is always located in the first groove portion 42 of the sliding means 40 and is accordingly also fixed axially to the housing 2. In this respect, the lancing carriage part 13 scarcely changes its position in this case.

According to the illustration of FIG. 3, the lancing device 1 is shown shortly before the proper lancing operation is triggered. If then the triggering actuation element 50 is pressed in the radial direction 52, the holding element 35 or respectively the spring part 41 thereof is displaced in the direction of the second groove portion 43. If the spring part 41 is at the level of the second groove portion 43, it can move in the lancing direction 25. In this respect, the lancing carriage element 13, driven by the lancing spring element, shoots in the lancing direction 25 and the lancing for taking a blood sample occurs.

If the triggering actuation element 50 is pressed further through in the radial direction 52, virtually at the same time, since it is substantially a uniform triggering-operation movement, the latching element 30 is moved out of its latching position. In this case, the spring-tensioning carriage part 12, owing to the spring force of the restoring spring element, does not yet however shoot back into its initial position (see FIG. 1), but remains in the tensioning position 28 for a while, since the spring-tensioning carriage part 12 is still simultaneously held securely by means of the triggering actuation element 50. Only by releasing the triggering actuation element 50 the spring-tensioning carriage part 12 is displaced back, as is shown with respect to the starting position 27 (see FIG. 1). In this respect, the spring force of the lancing spring element can be made available substantially completely for the proper lancing operation.

Further views of the lancing device 1 described above are illustrated in the illustrations of FIGS. 4 to 6. In order in particular to avoid repetition, no additional description of FIGS. 4 to 6 will be given.

The further lancing device 101 shown in FIGS. 7 and 8 has substantially an identical drive means 110 with a carriage unit 111 comprising a spring-tensioning carriage part 112 and a lancing carriage part 113, and with a dual spring oscillation system (not numbered here), as shown in the above FIGS. 1 to 6. In this respect, with regard to the construction, reference is made to the lancing device 1 of FIGS. 1 to 6, and only the essential differences will be described below.

The essential differences from the lancing device 1 of FIGS. 1 to 6 are that a slide element 160 with a bevel 161 is formed on the spring-tensioning carriage part 112, by means of which element a spring part 141 of a holding element (not shown here) of the lancing carriage part 113 is displaceable from a first groove portion 142 for axially fixing the spring-tensioning carriage part 112 into a second groove portion 143 of a sliding means 140. For this, the spring part 141 projects laterally over a longitudinal wall 162 provided on the lancing device 101, so that the bevel 161 of the slide element 160 can interact with the spring part 141, in particular if the spring-tensioning carriage part 112 is pressed in the lancing direction 125 by means of a tensioning actuation element 126 which is arranged axially on the rear side 129 of the lancing device 101.

If the spring part 141 is located in the second groove portion 143, the lancing device 101 can trigger, since the second groove portion 143 is arranged aligned with the longitudinal extension 105 and the lancing direction 125.

As can easily be seen, the tensioning actuation element 126 is immediately a triggering actuation element 150 within the meaning of the present invention, since by actuating the tensioning actuation element 126 the lancing device 101 can be triggered immediately if the latter is only pressed in far enough along the longitudinal extension 105 of the lancing device 101.

It goes without saying that the embodiments discussed above are merely first configurations of the lancing device according to the invention. In this respect, the configuration of the invention is not restricted to these embodiments.

LIST OF REFERENCE NUMERALS 1 lancing device
2 two-part housing
3 upper shell part
4 lower shell part
5 longitudinal extension
6 front side
7 lancet holder
8 lancet
10 drive means
11 carriage unit
12 spring-tensioning carriage part
13 lancing carriage part
14 first guide web
15 second guide web
16 lancing spring element receiving region
17 restoring spring element receiving region
18 front transverse wall
19 transverse wall
20 rear transverse wall
21 first longitudinal wall
22 second longitudinal wall
23 further longitudinal wall
25 lancing direction
26 tensioning actuation element
27 starting position
28 tensioning position
29 rear side
30 latching element
31 latching projection
32 latching edge
35 holding element
40 sliding means
41 spring part
42 first groove portion
43 second groove portion
50 triggering actuation element
51 parking position
52 radial direction
53 actuating finger element
54 actuating edge
66 lancing spring element
67 restoring spring element
101 lancing device
105 longitudinal extension
110 drive means
111 carriage unit
112 spring-tensioning carriage part
113 lancing carriage part
125 lancing direction
126 tensioning actuation element
129 rear side
140 sliding means
141 spring part
142 first groove portion
143 second groove portion
150 triggering actuation element
160 slide element
161 bevel
162 longitudinal wall

The invention claimed is:

1. A lancing device for taking blood samples, comprising a housing and a lancet holder for holding an exchangeable lancet and comprising a drive means for driving the lancet holder, in which the drive means has two spring elements comprising a lancing spring element for accelerating the lancet holder in a lancing direction and a restoring spring element for accelerating the lancet holder counter to the lancing direction and thereby providing a restoring movement of the lancet holder after the lancing operation, wherein the lancing spring element is positioned between the restoring spring element and the lancing holder with respect to the lancing direction,
   wherein the drive means has a carriage unit with a spring-tensioning carriage part and with a lancing carriage part, and the spring-tensioning carriage part and the lancing carriage part are arranged to be displaceable in translation relative to one another and form a lancing spring element receiving region and a restoring spring element receiving region, and the lancing spring element receiving region can be reduced by translational displacement of the spring-tensioning carriage part relative to the lancing carriage part into a first tensioning position in order to pre-tension the lancing spring element within the lancing spring element receiving region for a forthcoming lancing operation,
   the spring-tensioning carriage part being arranged to be movable manually into the tensioning position by a tensioning actuation element from outside the lancing device, wherein the spring-tensioning carriage part comprises a latching element for latching in a tensioning position in which the lancing spring element is pre-tensioned such that the lancing carriage part can be accelerated for the lancing operation, and the lancing carriage part comprises a holding element for holding the lancing carriage part in a second, tensioning position, wherein the second tensioning position is different from the first tensioning position, in which the lancing spring element is pre-tensioned such that the lancing carriage part can be accelerated for the lancing operation,
   wherein said holding element of the lancing carriage part and said latching element of the spring-tensioning carriage part are arranged to be unlocked sequentially,
   wherein said tensioning actuation element is arranged to be pressed into the housing of the lancing device in the lancing direction to move the spring-tensioning carriage part into said first tensioning position in order to be able to pre-tension the lancing spring element.

2. The lancing device according to claim 1, wherein a triggering actuation element is displaceable manually out of a parking position into a triggering position in which both the lancing carriage part and the spring-tensioning carriage part are unlocked, wherein the spring-tensioning carriage part is held in the tensioning position by the triggering actuation element in the triggering position of the triggering actuation element.

3. The lancing device according to claim 2, wherein the triggering actuation element is arranged radially in front of the latching element of the spring-tensioning carriage part and in front of the holding element of the lancing carriage part such that, owing to the triggering actuation element, on the one hand the latching element is arranged to be displaceable out of its latching position and on the other hand the holding element is arranged to be displaceable out of the holding position.

4. The lancing device according to claim 3, wherein the latching element can be engaged on a latching edge of the housing of the lancing device.

5. The lancing device according to claim 4, wherein the holding element is mounted to be guided both radially and axially along a sliding means, the sliding means being arranged adjacent to the lancing carriage part.

6. The lancing device according to claim 3, wherein the holding element is mounted to be guided both radially and axially along a sliding means, the sliding means being arranged adjacent to the lancing carriage part.

7. The lancing device according to claim 3, wherein the latching element and the holding element being arranged axially directed at each other.

8. The lancing device according to claim 2, wherein the tensioning actuation element is arranged axially behind the carriage unit on an end of the lancing device which is remote from the lancet holder, and the triggering actuation element is arranged radially next to the carriage unit.

9. The lancing device according to claim 2, wherein the latching element and the holding element being arranged axially directed at each other.

10. The lancing device according to claim 1, wherein the latching element and the holding element being arranged axially directed at each other.

11. The lancing device according to claim 10, wherein the latching element can be engaged on a latching edge of the housing of the lancing device.

12. The lancing device according to claim 10, wherein the holding element is mounted to be guided both radially and axially along a sliding means, the sliding means being arranged adjacent to the lancing carriage part.

13. The lancing device according to claim 1, wherein the lancing spring element receiving region is limited at the front by an axially slidable lancing carriage part partition and at the rear by an axially slidable spring-tensioning carriage part partition.

14. The lancing device according to claim 1, wherein the spring-tensioning carriage part is arranged at least partially within the lancing carriage part.

* * * * *